US012575947B2

(12) United States Patent
Dawson et al.

(10) Patent No.: US 12,575,947 B2
(45) Date of Patent: Mar. 17, 2026

(54) PROSTHESIS COUPLING, A SOCKET COUPLING, A ROTARY CONNECTOR CORE AND A COMPLIANT MOUNTING ELEMENT

(71) Applicant: Taska Prosthetics Limited, Christchurch (NZ)

(72) Inventors: Ross Hughan Dawson, Christchurch (NZ); Mathew James Jury, Wellington (NZ); David Neil Lovegrove, Christchurch (NZ); Michael James Van Der Werff, Christchurch (NZ); Matthew Sultan Yan, Christchurch (NZ)

(73) Assignee: Taska Prosthetics Limited, Christchurch (NZ)

( * ) Notice: Subject to any disclaimer, the term of this patent is extended or adjusted under 35 U.S.C. 154(b) by 681 days.

(21) Appl. No.: 17/905,454

(22) PCT Filed: Mar. 1, 2021

(86) PCT No.: PCT/NZ2021/050032
§ 371 (c)(1),
(2) Date: Sep. 1, 2022

(87) PCT Pub. No.: WO2021/177840
PCT Pub. Date: Sep. 10, 2021

(65) Prior Publication Data
US 2023/0140396 A1     May 4, 2023

(30) Foreign Application Priority Data
Mar. 2, 2020    (NZ) ........................................ 762173

(51) Int. Cl.
A61F 2/58 (2006.01)
A61F 2/50 (2006.01)
A61F 2/80 (2006.01)

(52) U.S. Cl.
CPC ................ A61F 2/585 (2013.01); A61F 2/80 (2013.01); *A61F 2002/5069* (2013.01)

(58) Field of Classification Search
CPC ..... A61F 2/585; A61F 2/80; A61F 2002/5069
See application file for complete search history.

(56) References Cited

U.S. PATENT DOCUMENTS 3,900,900 A     8/1975  Horvath et al.
4,010,495 A     3/1977  Horvath
(Continued)

FOREIGN PATENT DOCUMENTS

GB          550886 A     1/1943
GB         2129086 A     5/1984
(Continued)

OTHER PUBLICATIONS

Supplementary European Search Report for Patent Application No. EP 21763561 (Jun. 23, 2023).
(Continued)

*Primary Examiner* — Nitin Patel
(74) *Attorney, Agent, or Firm* — Fish & Richardson P.C.

(57) ABSTRACT

A rotatable and removable wrist connection for a prosthetic hand. A prosthesis coupling includes first and second ball race sections that may be moved together or apart to constrain ball bearings to an inner zone or an outer zone to allow the prosthesis coupling to be secured to or removed from a socket coupling. A socket coupling includes a socket body for receiving a wrist coupling having a rotary connector core extending from the socket body and compliantly mounted to the socket body.

25 Claims, 14 Drawing Sheets

(56) References Cited

U.S. PATENT DOCUMENTS

| | | | |
|---|---|---|---|
| 4,613,331 | A | 9/1986 | Jacobsen et al. |
| 7,297,002 | B2 | 11/2007 | Kostrzewski et al. |
| 10,369,024 | B2 | 8/2019 | Gill |
| 2007/0173955 | A1 | 7/2007 | Archer et al. |
| 2007/0260328 | A1* | 11/2007 | Bertels ..................... A61F 2/70 623/59 |
| 2008/0195206 | A1 | 8/2008 | Chee et al. |
| 2009/0076614 | A1 | 3/2009 | Arramon |
| 2013/0195540 | A1* | 8/2013 | Wozencroft ............. A61F 2/78 403/83 |
| 2018/0036145 | A1 | 2/2018 | Jury et al. |
| 2018/0064563 | A1 | 3/2018 | Gill |
| 2019/0091040 | A1 | 3/2019 | Gill et al. |
| 2019/0343661 | A1* | 11/2019 | Messner ................ A61B 5/273 |
| 2021/0330479 | A1* | 10/2021 | Reyes .................... A61F 2/585 |

FOREIGN PATENT DOCUMENTS

| | | | |
|---|---|---|---|
| JP | 07-004396 | B2 | 1/1995 |
| JP | 2003-088539 | A | 3/2003 |
| TW | M257179 | U | 2/2005 |
| WO | WO-2011094602 A1 * | 8/2011 | .............. A61F 2/76 |
| WO | 2014/027897 A1 | 2/2014 | |
| WO | 2017/061879 A1 | 4/2017 | |

OTHER PUBLICATIONS

"MC Standard ETD Prosthetist Manual", available on the internet at: https://fillauer.com/wp-content/uploads/2019/12/1910016-PROSTHETIST-MANUAL-MC-Standard-ETD-Rev-H-08-07-2019-F.pdf. (2019).

"MC Waterproof Collar for Quick Disconnect Wrist Prosthetist Manual" available on the internet at: https://fillauer.com/wp-content/uploads/2019/12/1910112-PROSTHETIST-MANUAL-MC-Waterproof-Quick-Disconnect-Rev- A-09-18-2019-F.pdf (2019).

International Preliminary Report on Patentability for PCT/NZ2021/050032 (Sep. 6, 2022).

Bebionic3 Technical Information, "Wrist Options", Bebionic, 2012, RSLLIT317 Issue 2, Part 4.1, p. 28-29.

Otto Bock, "Greifer 8E26", The Journal of the International Society for Prosthetics and Orthotics, 1981, 5(3): 2.

International Search Report and Written Opinion for PCT/NZ2021/050032 mailed Jun. 7, 2021. (17 pages).

Office Action in Japanese Appln. No. 2022-550899, mailed on Nov. 11, 2025, 5 pages (with English translation).

* cited by examiner

107

108

PROSTHESIS COUPLING, A SOCKET COUPLING, A ROTARY CONNECTOR CORE AND A COMPLIANT MOUNTING ELEMENT

CROSS-REFERENCE-TO-RELATED-APPLICATION(S)

This application is a National Stage Application of PCT/NZ2021/050032, filed Mar. 1, 2021, which claims benefit of priority to New Zealand Application No. 762173, filed Mar. 2, 2020, and which applications are incorporated herein by reference. To the extent appropriate, a claim of priority is made to each of the above disclosed applications.

FIELD OF THE DISCLOSURE

The present disclosure relates to a rotatable and removable wrist connection for a prosthetic hand of the type commonly referred to as a Quick Wrist Disconnect (QWD).

BACKGROUND

Prosthetic limbs are typically attached to a user's stump via a socket which conforms to the shape of the stump. A connector may be provided to allow the prosthesis to be attached and detached from the stump. In the case of a wrist it is desirable for the prosthetic limb to be both rotatably coupled and easily connected to and removed from a stump. Additionally, for an automated hand, signals need to be conveyed through the connector to the hand.

In the 1970's Otto Bock developed a rotatable and removeable prosthetic connector, as described in U.S. Pat. No. 3,900,900, that has become the industry standard and is commonly referred to as a Quick Wrist Disconnect (QWD) connector. A prothesis coupling component is secured to the prosthetic limb and a socket coupling component is secured to a socket secured to a patient's stump. The prothesis coupling and socket coupling may be engaged by being pushed together such that they are then axially locked together. The prosthesis can then be rotationally positioned by the user via a detent mechanism in the coupling until the prosthesis is rotated through about 330 degrees to allow release.

By virtue of the rotational positioning and the release mechanism actuation requiring the same action by the user, the standard QWD may suffer from accidental release, potentially exposing a user to risk or damaging an expensive prosthetic limb. The standard QWD may suffer from accidental release, potentially exposing a user to risk or damaging an expensive prosthetic limb. Further, the push locking arrangement may not move the movable snap ring of the socket coupling sufficiently to ensure that the prosthesis coupling and socket coupling are locked together, again potentially exposing a user to risk or damaging an expensive prosthetic limb.

For an automated hand a rotary connector core is rigidly mounted to the socket coupling and this may be subject to damage as the rotary connector core is inserted into a rotary connector housing of a prosthesis socket before mechanical coupling occurs. The connection between a rotary connector core and a socket coupling may also not be waterproof which may allow water to enter and interfere with signals or damage electrical or electronic components. Further, rotary connector cores are typically molded which is complex and expensive and does not easily allow variation.

SUMMARY

In a prosthetic QWD connector it is desirable for any new QWD design to be backwards compatible with the industry standard QWD connector. This creates challenges due to features of the existing QWD design, the need for a rotatable coupling and the very limited available space. The prosthetic QWD connector disclosed herein can have any of the following and/or other advantages.

The present disclosure provides examples of prosthetic QWD connectors that are compact, have lower risk of accidental release, provide positive locking and allow easy release whilst providing backwards compatibility with the industry standard QWD connector.

The present disclosure also provides examples of prosthetic QWD connectors including a compliantly mounted rotary connector core capable of allowing movement of the rotary connector core with respect to the socket coupling, thus allowing certain forces during coupling to be absorbed without damaging the rotary connector core whilst also providing a waterproof seal between a socket coupling.

The examples above can provide a QWD connector that is backwards compatible with standard QWD connectors whilst offering one or more of the advantages outlined above.

In some configurations, a prosthesis coupling can be configured to rotatably and releasably engage with a race of a socket coupling and comprise: a first sleeve including a first annular ball race section; a second sleeve having a second annular ball race section; and bearings provided within a race formed by the first ball race section and the second ball race section, wherein the first and second sleeves may be relatively moved such that: in a first configuration, in which the first ball race section and the second ball race section are brought together, the bearings are constrained to an outer annular zone, preventing removal of the prosthesis coupling when engaged with a socket coupling; and in a second configuration, in which the first ball race section and the second ball race section are moved apart, the bearings may move to an inner annular zone, allowing removal of the connector from a socket.

In some configurations, the prothesis coupling can be configured to rotatably and releasably engage with a race of a socket coupling and comprise: a body having an annular section; a first annular ball race section provided on the annular section; a second annular ball race section movable between first and second positions on the annular section: bearings provided within a race formed by the first ball race section and the second ball race section; and a release actuator movable in a first direction with respect to the body to move the second annular ball race section between: a first configuration in which the first ball race section and the second ball race section are brought together such that the bearings are constrained to an outer annular zone, preventing removal of the connector when engaged with a socket coupling; and a second configuration in which the first ball race section and the second ball race section are moved apart such that the bearings may move to an inner annular zone, allowing removal of the prosthesis coupling from a socket coupling.

In some configurations a socket coupling can include a socket body for receiving a wrist coupling having a rotary connector core extending from the socket body wherein the rotary connector core is compliantly mounted to the socket body.

In some configurations a rotary connector core can include a compliant mounting element.

In some configurations a compliant mounting element can be configured to engage with a socket coupling and a rotary connector core so as to allow movement between the socket coupling and rotary connector core about the compliant mounting element.

In some configurations a rotary connector core can comprise a plurality of stacked sections consist of alternating conductive sections and insulating sections tensioned together to maintain a cylindrical form by a tensioning element between the top and bottom of the stack.

In some configurations a socket body can include a compliant mounting element.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below. In the examples below ball bearings are employed but it will be appreciated that non-spherical bearings, such as roller bearings could be employed.

Example Prosthesis Coupling

Figure 1:
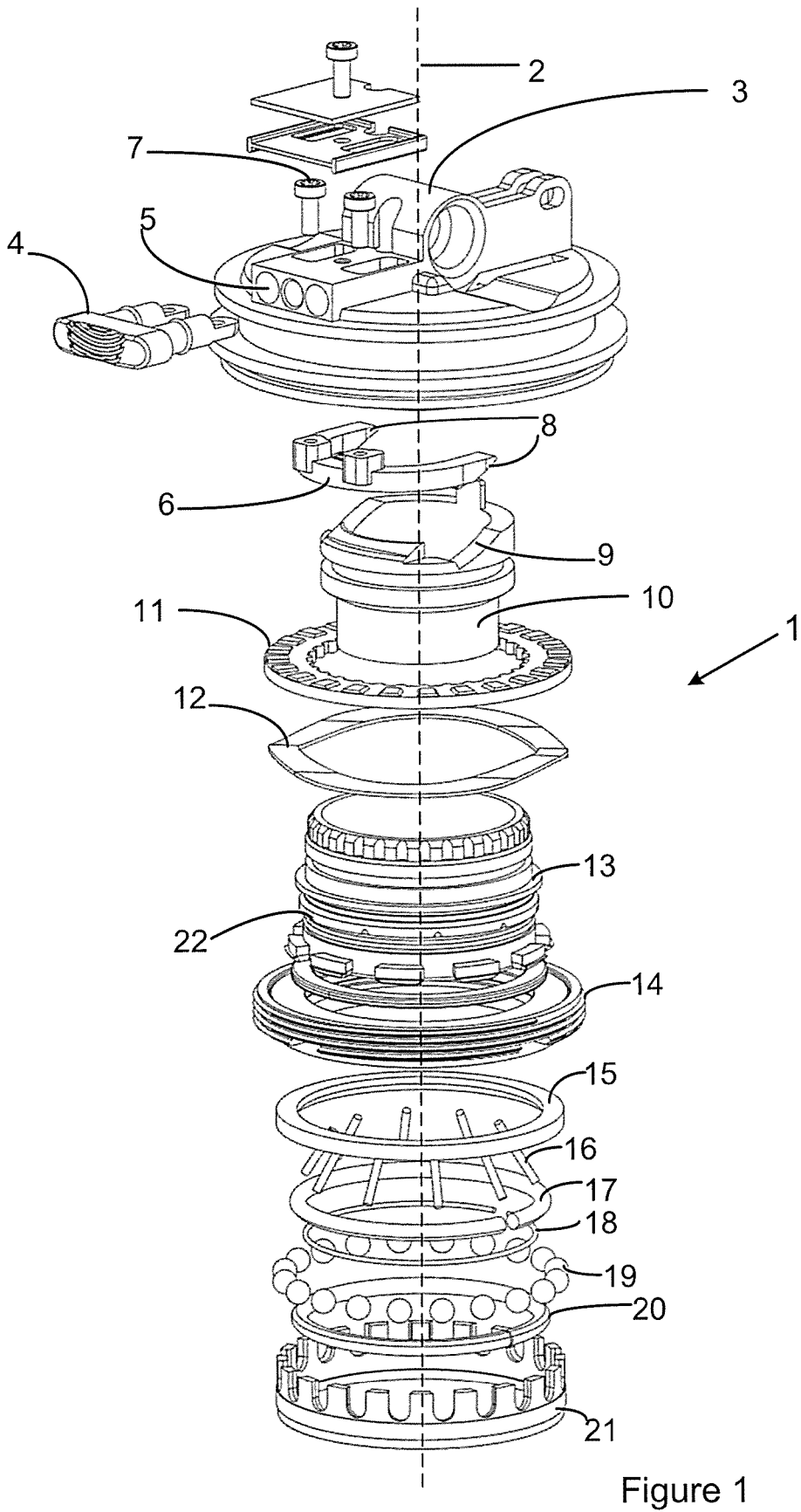
FIG. 1 shows an exploded view of the components of a first example prosthesis coupling.
Figures 2, 3, 4:
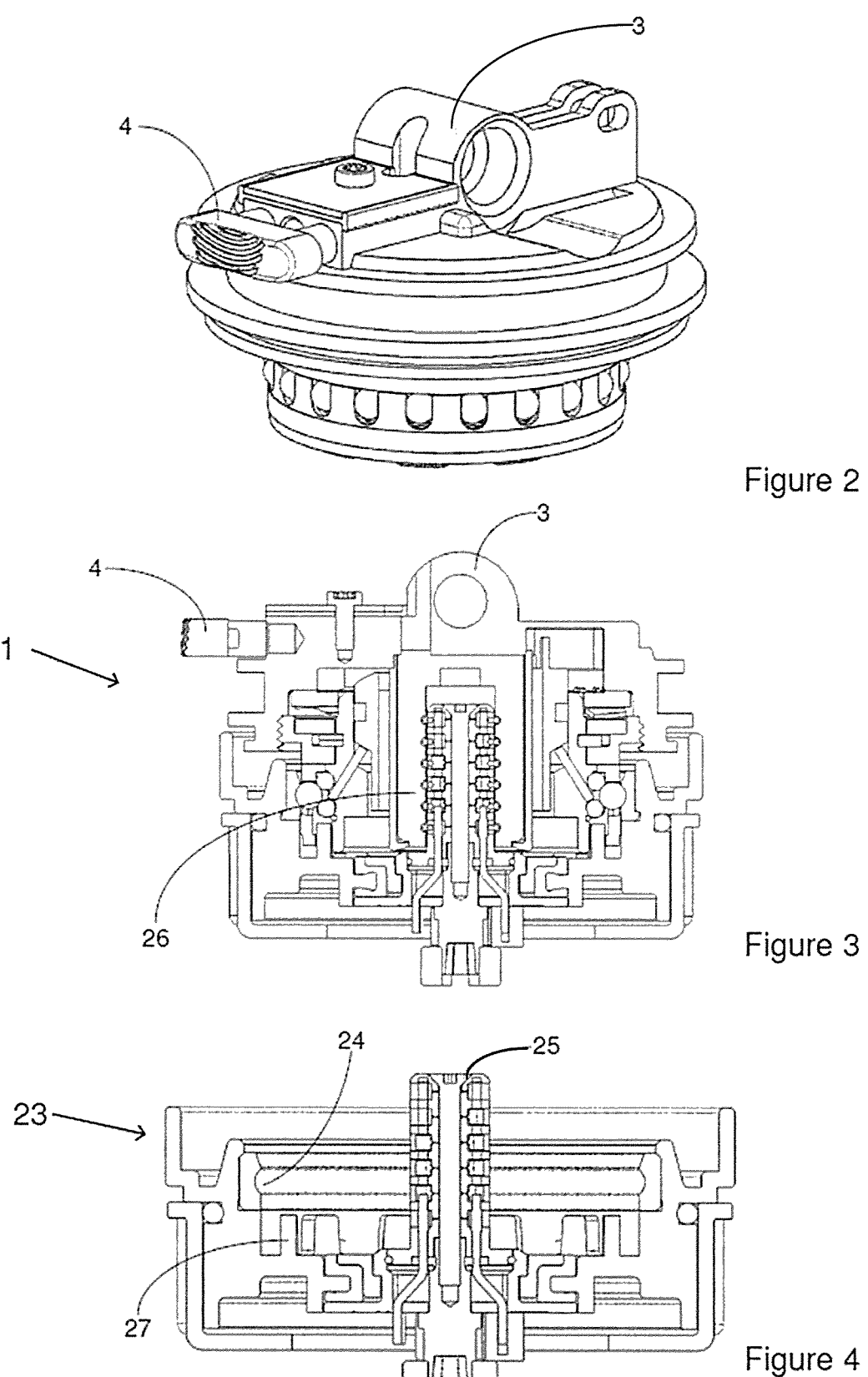
FIG. 2 shows a top perspective view of an assembled prosthesis coupling of the components shown in FIG. 1.
FIG. 3 shows a cross-sectional view of the prosthesis coupling of FIG. 2.
FIG. 4 shows a cross-sectional view of a socket coupling for receiving the prosthesis coupling of FIGS. 1 to 3.

The present disclosure provides examples of a prothesis coupling for rotatable and releasable connection to a socket connector. FIGS. 1 to 3 show a first example prosthesis coupling 1 having an axis 2. An interface plate 3 allows attachment to a prosthetic limb. A button 4 locates within apertures 5 and is movable laterally with respect to the axis 2. Button 4 is secured to ramp plate 6 by screws 7. When button 4 is depressed ramp plate 6 moves inwards, moving ramps 8 towards ramp surfaces 9 of annular inner sleeve 10.

A castellated ring 11 and wave spring 12 are provided about main body annular sleeve 13. Annular sleeve 13 provides an annular body for mounting the snap rings and detent as described below. Snap ring retainer 15 is mounted to main sleeve body 13 to retain static snap ring 17 in place. Detent ring 18 is mounted on main sleeve body 13 so as to define two annular regions in which dynamic snap ring 20 may be positioned about sleeve body 13, as will be described below. Inner sleeve 10 may act on pins 16, located in apertures 22 of main sleeve body 13, to move dynamic snap ring 20 from an upper to a lower position.

The snap rings 17 and 20 provide ball race sections defining a ball race constraining the longitudinal movement of bearings 19 in the direction of axis 2. Bearing cage 21 retains the bearings radially within it.

FIG. 3 shows a cross-sectional view of an assembled prosthesis coupling 1 as shown in FIGS. 1 and 2 (engaged with a socket coupling) with a standard QWD socket coupling shown alone below in FIG. 4. When the prosthesis coupling 1 and socket coupling 23 are locked together ball bearings 19 run in track 24 of socket coupling 23 and rotary connector core 25 couples with rotary connector housing 26 to allow electrical signals to pass from socket coupling 23 to prothesis coupling 1. Bosses 27 assist in locking the dynamic snap ring 20 in its locked position as will be described below.

Prior to attachment of a prosthesis coupling to a socket coupling the dynamic snap ring is in the position 20' shown in FIG. 6, below detent ring 18, which allows the ball bearings to move inwardly to pass the race 24 of a socket coupling. As prosthesis coupling 1 is urged towards socket coupling 23 bosses 27 force dynamic snap ring 20 up from position 20', within a first annular recess below detent 18, over detent ring 18, to position 20 within a second annular recess below detent 18. As the dynamic snap ring 20 moves to this upper position the distance between the dynamic snap ring 20 and the static snap ring 17 decreases and the ball bearings 19 are forced outwards into race 24 of socket coupling 23 so as to retain the prosthesis coupling to the socket coupling, due to the constrained positions of the ball bearings, whilst allowing relative rotation.

Figures 5, 6:
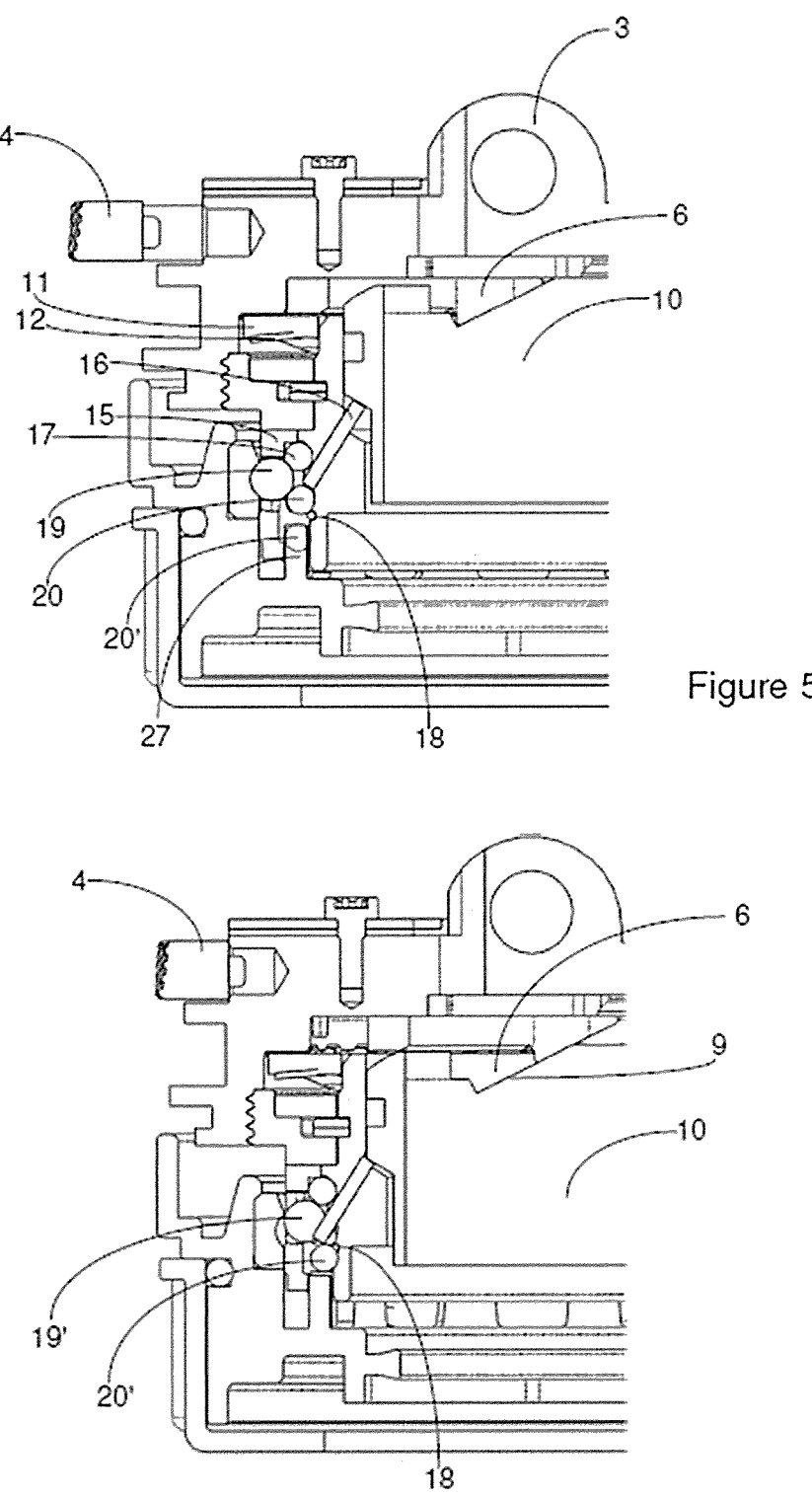
FIG. 5 shows a partial section of FIGS. 1 to 4 illustrating locking of the prosthesis coupling to a socket coupling.
FIG. 6 shows a partial section of FIGS. 1 to 4 illustrating unlocking of the prosthesis coupling from a socket coupling.
Figure 7:
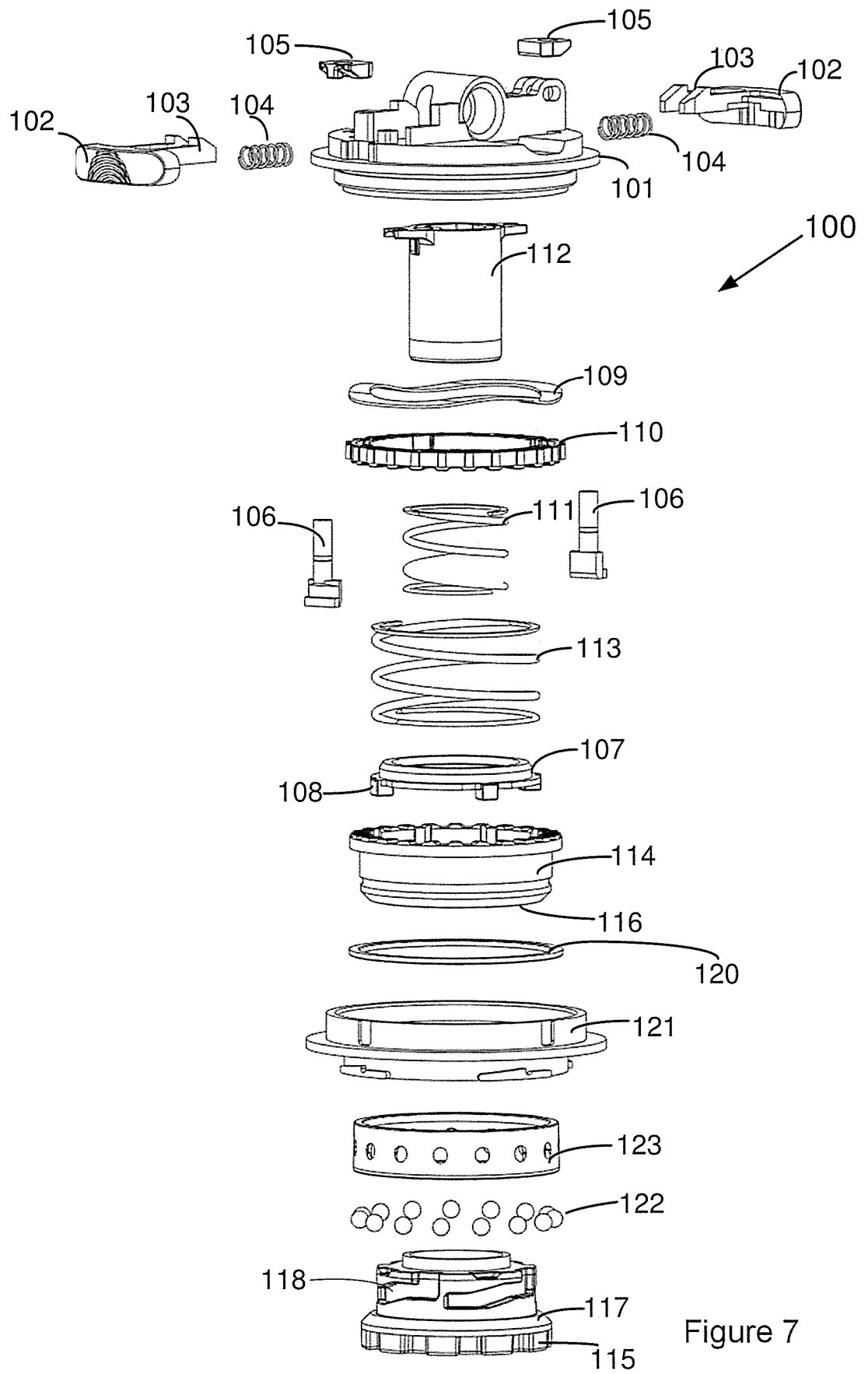
FIG. 7 shows an exploded view of the components of a second example prosthesis coupling.
Figures 8, 9:
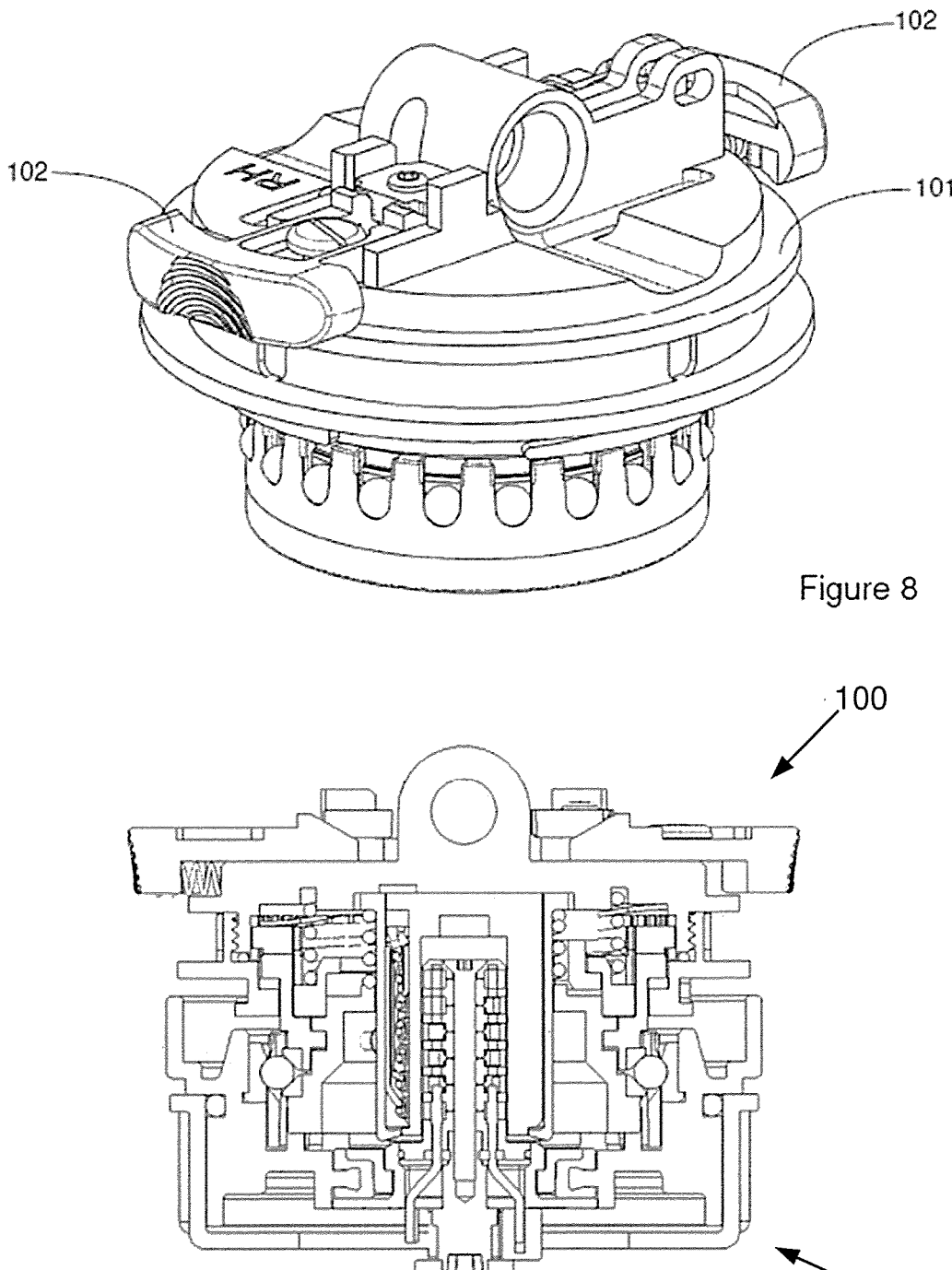
FIG. 8 shows a top perspective view of the prosthesis coupling of FIG. 7 assembled from the components shown in FIG. 7.
FIG. 9 shows a cross-sectional view of the prosthesis coupling of FIGS. 7 and 8.
Figure 10:
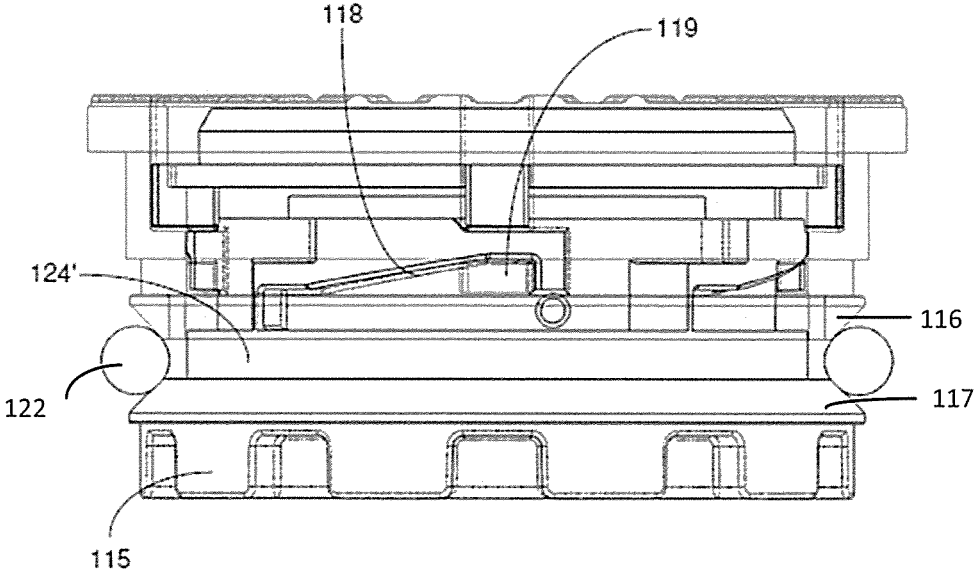
FIG. 10 shows the prosthesis coupling of FIGS. 7 to 9 in an unlocked configuration.

Referring now to FIG. 6 disengagement of prosthesis coupling 1 from socket coupling 23 will be described. A release actuator is provided by button 4, ramp plate 6 and inner sleeve 10. Push button 4 may be recessed within interface plate 3 to avoid accidental actuation. When push button 4 is depressed ramp plate 6 is moved inwards, lateral to axis 2, against ramp surface 9 of inner sleeve 10. This forces inner sleeve 10 down, forcing pins 16 down, which in turn forces dynamic snap ring 20 down over detent 18 to position 20'. With dynamic snap ring 20 in position 20' the ball bearings may move inwardly to positions 19', which allows the ball bearings to move out of race 24, thus allowing the prosthesis coupling 1 to be removed from socket coupling 23. The bosses 27 do not prevent the dynamic slip ring 20 moving down as the prosthesis coupling moves up as inner sleeve body 10 is forced down.

It will be appreciated that other actuation mechanisms may be employed where a release element is moved relative to the prosthesis coupling to effect release. Instead of being pushed in, ramp plate 6 could be rotated about axis 2 via a lever projecting outward from ramp plate 6. In this arrangement one of ramps 8 would be oppositely inclined to that shown, as would a corresponding ramp surface 9. In another example a cam may be rotated by a lever in a plane through axis 2 with the cam acting upon inner sleeve 10 to move it downwards to effect release.

Referring now to FIGS. 7 to 12 a second example prosthesis coupling will be described. Prosthesis coupling 100 includes an interface plate 101 having a pair of push buttons 102 on either side having ramps 103 at their distal ends. The push buttons 102 are slidably mounted with respect to the interface plate 101 and biased outwardly by springs 104. Ramps 105 are secured to lifters 106 which can lift locking ring 107 when the push buttons 102 are depressed. Wave spring 109 and castellated ring 110 are provided below interface plate 101. Main compression spring 111 is provided about barrel 112 to bias the outer sleeve 114 downwards. Lock ring compressing spring 113 is positioned to bias locking ring 107 downwards.

In this example an outer sleeve 114 is rotatably engaged about an inner sleeve 115 with ball race sections 116 and 117 of each sleeve forming a ball race. In this example the spacing between ball race sections 116 and 117 is adjusted by relative axial displacement between the inner and outer sleeves. This axial displacement could be achieved by pure axial displacement or with rotation, as described in the example below. In this example a number of ramps 118 are provided on inner sleeve 115 which engage with projections 119 of outer sleeve 114. It will be appreciated that instead of this construction inter-engaging threads (or partial threads) could be provided on the inner and outer sleeves.

A bushing 120 and threaded ring 121 are provided about outer sleeve 114. Ball bearings 122 are retained within a region defined by the axial separation of race sections 116 and 117 and the bearing cage 123. When outer sleeve 114 is rotated anti-clockwise projections 119 may ride up ramp 118 to create a large axial spacing 124' between race sections 116 and 117 (see FIG. 10) allowing bearings 122 to move inwardly into an inner annular zone and allow the prosthesis coupling to be connected to or disconnected from a socket coupling. When outer sleeve 114 is rotated clockwise projections 119 may ride down ramp 118 to create a smaller axial spacing 124 between race sections 116 and 117 (see FIG. 11) forcing ball bearings 122 to move outwardly to an outer annular zone such as to retain the prosthesis coupling to a socket coupling. It will be appreciated that the directions of relative rotation would be opposite if the ramp sections were oppositely inclined. The relative axial displacement between the race sections 116 and 117 thus allows two configurations: a first configuration in which the first ball race section 116 and the second ball race 117 section are brought together such that the bearings are constrained to an outer annular zone, preventing removal of the connector when engaged with a socket coupling; and a second configuration in which the first ball race section 116 and the second ball race section 117 are moved apart such that the bearings may move to an inner annular zone, allowing removal of the prosthesis coupling from a socket coupling.

To prevent accidental release relative rotation between sleeves 114 and 115 to separate the race sections 116 and 117 (i.e. from the configuration shown in FIG. 11 to the configuration shown in FIG. 10) may require a release of a locking mechanism. The locking mechanism could consist of one or more pins passing through apertures in the inner and outer sleeves in the configuration shown in FIG. 11, which may be removed to allow rotation to the configuration shown in FIG. 10. Such pins may be of any desired cross-section or shape and simply need to engage apertures in the sleeves to prevent rotation. Alternatively, a locking mechanism may require rotation of an element relative to the interface plate 101 to allow relative rotation between sleeves (a detent mechanism may also be included to avoid unintentional rotation of such a locking mechanism). Below an example locking mechanism employing a locking ring is described.

Figure 11:
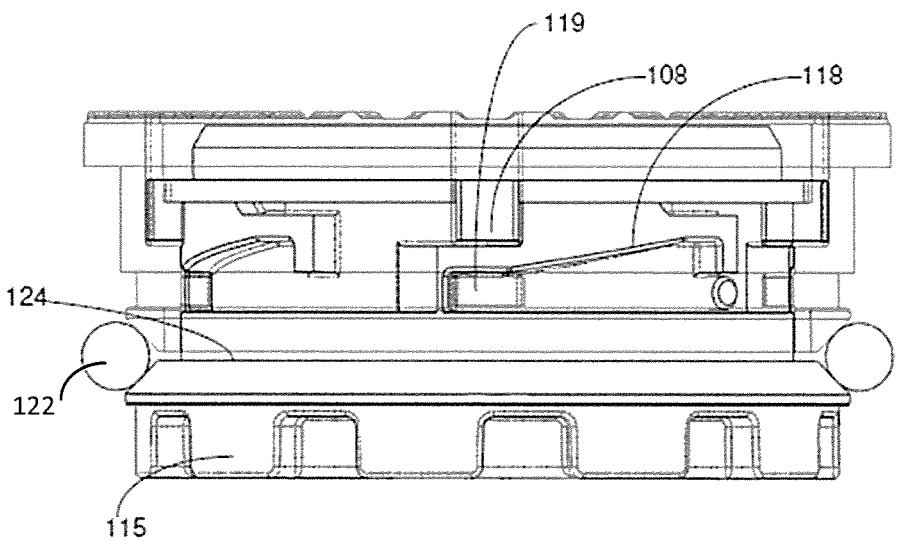
FIG. 11 shows the prosthesis coupling of FIGS. 7 to 9 in a locked configuration.
Figure 12:
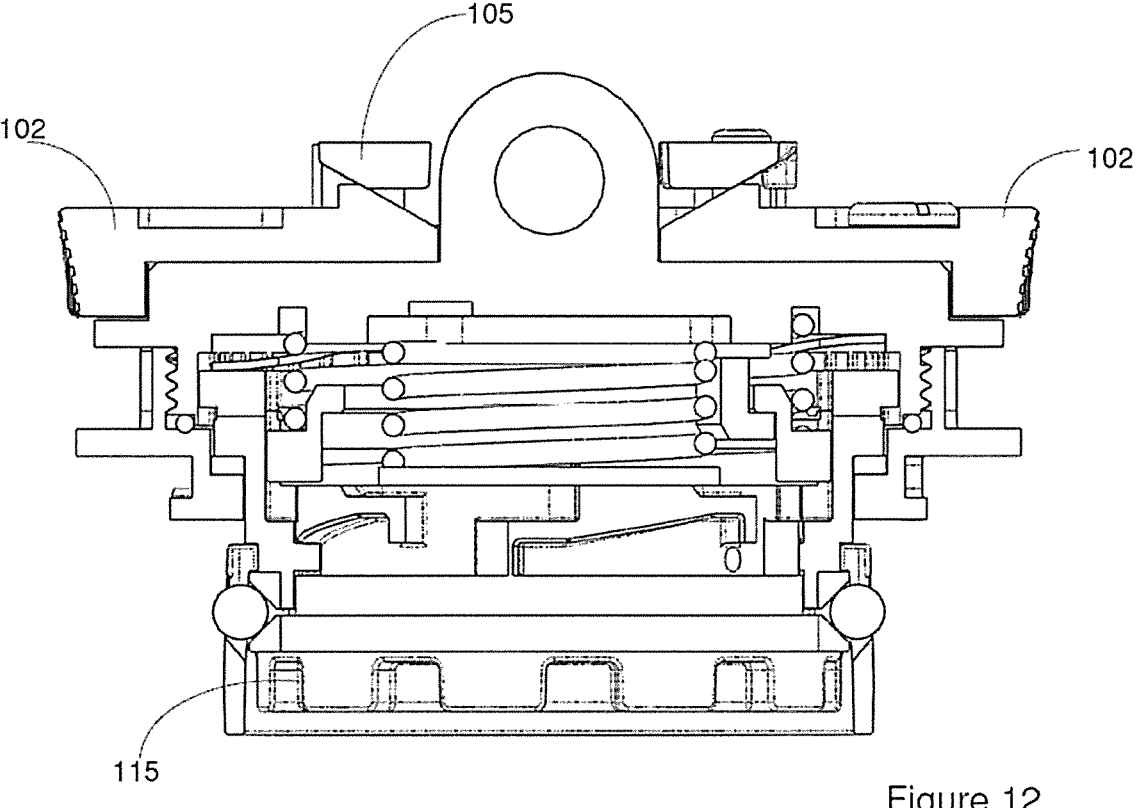
FIG. 12 illustrates unlocking of the prosthesis coupling of FIGS. 7 to 11 from a socket coupling.
Figure 13A:
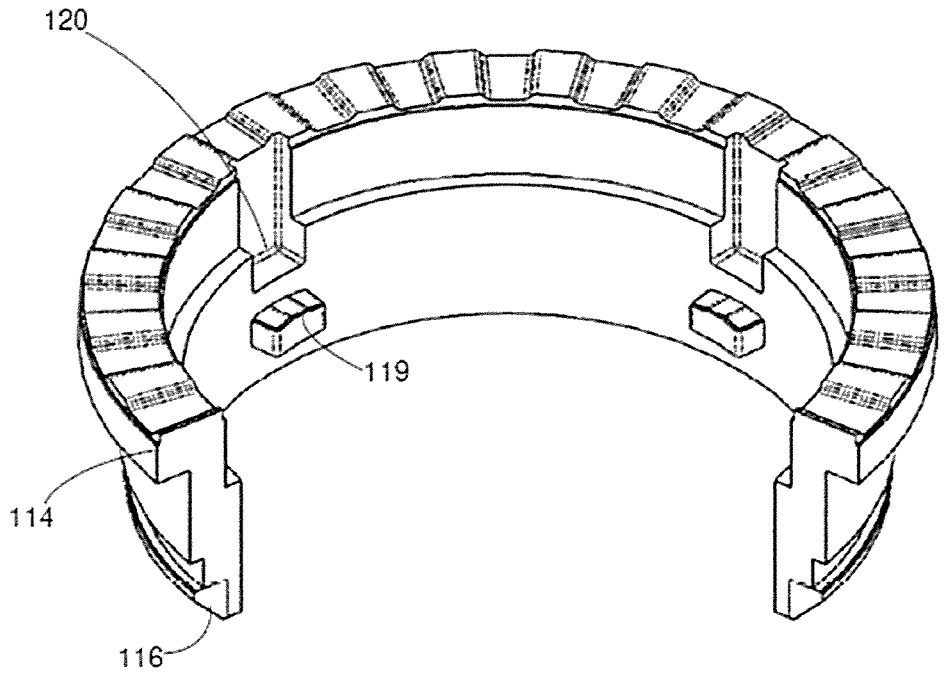
FIG. 13*a* shows a cutaway perspective view of the outer sleeve of the prosthesis coupling of FIGS. 7 to 12.
Figure 13B:
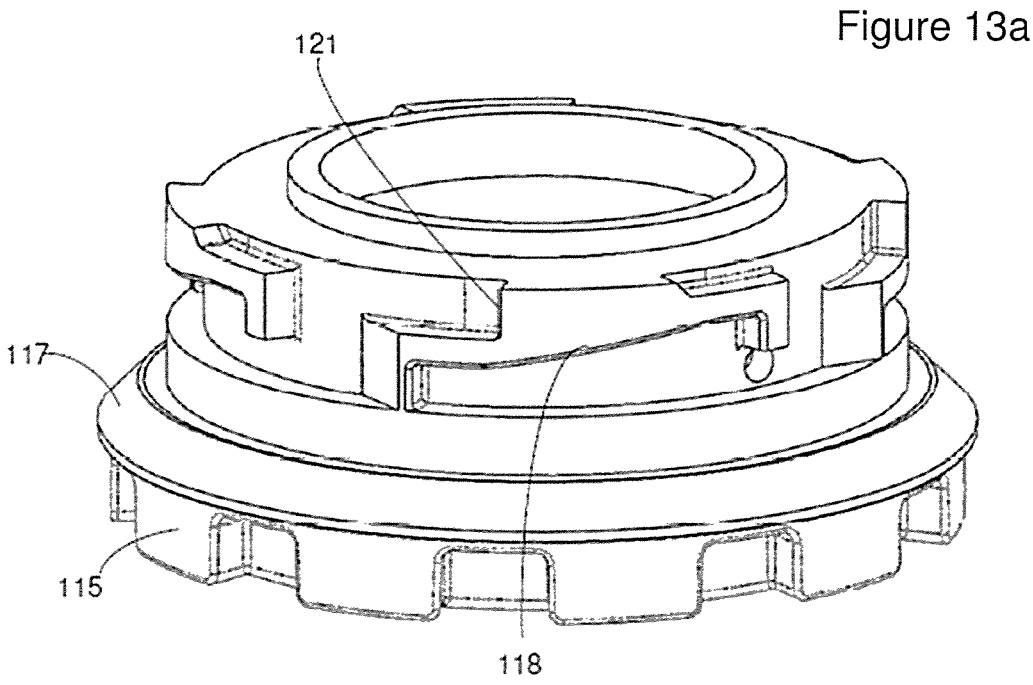
FIG. 13*b* shows a perspective view of the inner sleeve of the prosthesis coupling of FIGS. 7 to 12.
Figure 14:
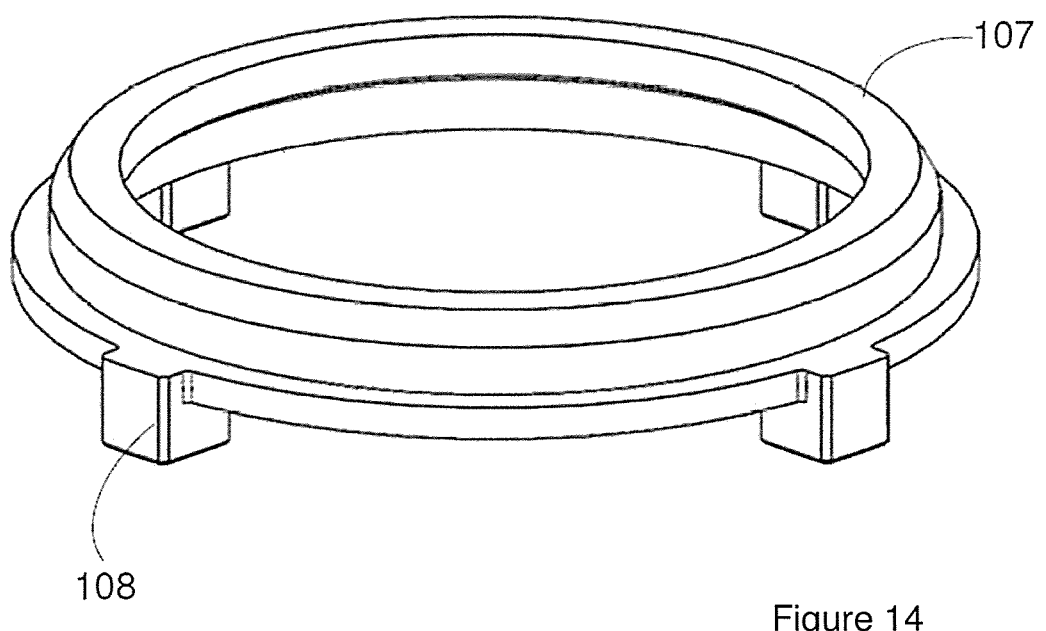
FIG. 14 shows a perspective view of the locking ring of the prosthesis coupling of FIGS. 7 to 12.

When the inner and outer sleeves have the configuration shown in FIG. 11 projections 108 of locking ring 107 engage in slots 120 in outer sleeve 114 and notches 121 in inner sleeve 115 (best shown in FIGS. 13a to 14) which prevent relative rotation between the sleeves when projections 108 are engaged, thus preventing separation of race sections 116 and 117 to permit release of the prosthesis coupling from the socket coupling. As illustrated in FIG. 12, when buttons 102 are pressed inwards ramps 103 act against ramps 105 to lift locking ring 107 via lifters 106 to remove projections 108 from slots 120 in outer sleeve 114 and notches 121 in inner sleeve 115 to permit relative rotation of the sleeves. Thus, upon depression of the buttons a prosthesis coupling may be rotated relative to a socket coupling (by about 45 degrees in this case) to allow release of the prosthesis coupling from a socket coupling.

Figures 15A, 15B, 15C:
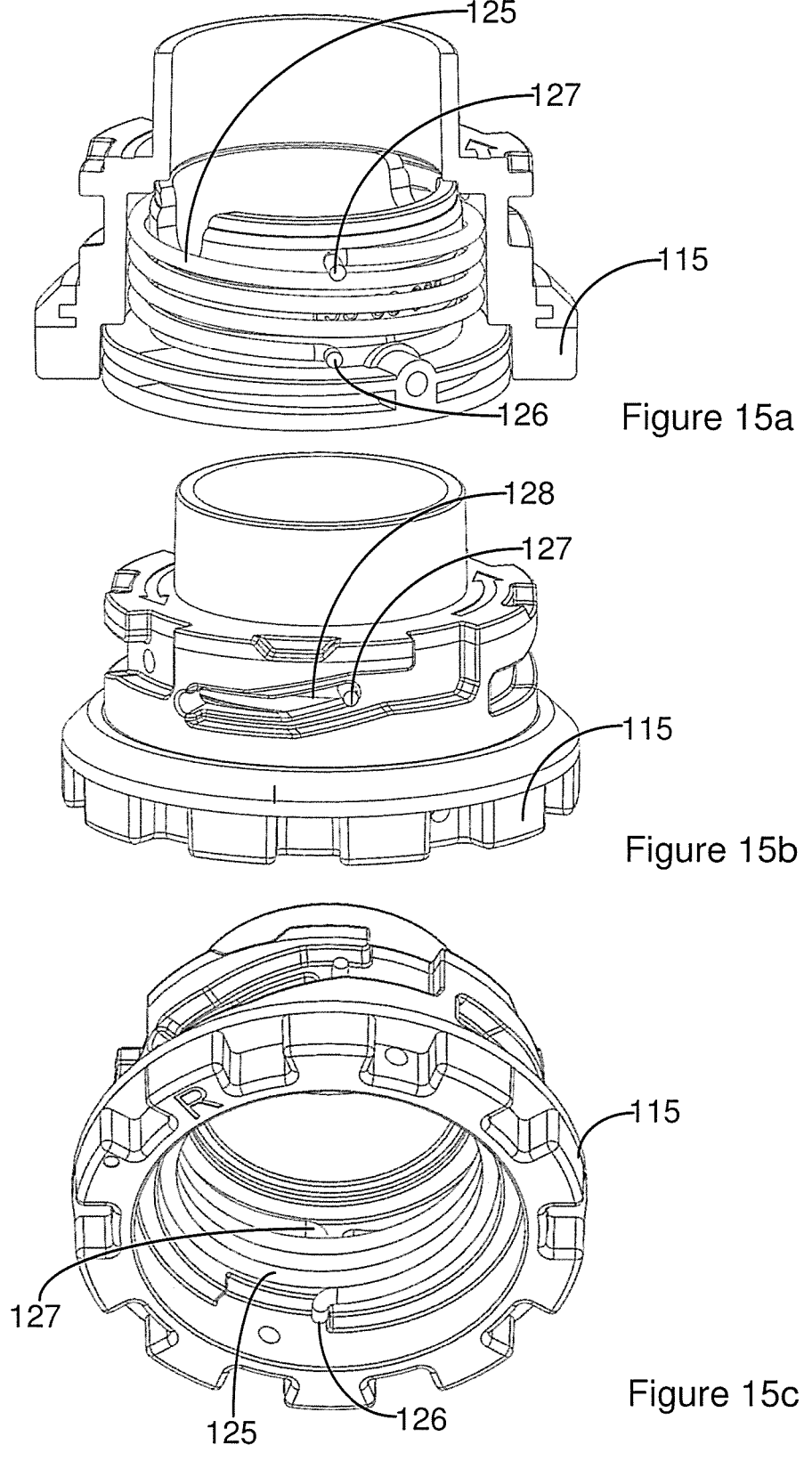
FIGS. 15*a* to 15*c* show a modified form of the second example prosthesis coupling including a biasing mechanism between the inner and outer sleeves.

If the prosthesis coupling of the second example is not correctly operated there is a risk that the first ball race section 116 and the second ball race 117 section may remain together when the prosthesis coupling is removed from a socket coupling such that the bearings are constrained to an outer annular zone, preventing future engagement with a socket coupling. With reference to FIGS. 15a to 15c a biasing means, in the form of a helical torsion spring 125, is provided to causes relative rotation between the inner sleeve 115 and outer sleeve 114 to urge them towards the second configuration (race sections 116 and 117 moved apart), when the locking mechanism does not prevent relative rotation. In this way when the prothesis coupling is removed from a socket coupling the ball race may easily return to the second configuration, allowing attachment to a socket coupling.

It will be appreciated that a range of biasing means may be employed including extension, compression or torsional biasing elements and a helical torsion spring is given by way of non-limiting example.

Referring to the example of FIGS. 15a to 15c a helical torsion spring 125 is provided within inner sleeve 115. A first leg of helical torsion spring 125 engages with an aperture in inner sleeve 115. A second leg 127 of helical torsion spring 125 passes through a slot 128 in inner sleeve 115 and engages with an aperture in outer race 114. The configuration is such that the helical torsion spring 125 rotates the inner sleeve 115 with respect to the outer sleeve 114 towards the second configuration, when the locking mechanism does not prevent relative rotation. In this way race sections 116 and 117 may easily return to the second configuration when removed from a socket coupling to allow easy future engagement with a socket coupling.

Referring to FIGS. 16 to 19 examples of a compliant mount, rotary connector and socket coupling will be described. As shown in the exploded view of a rotary connector core in FIG. 19 the rotary connector core 200 can be formed by alternately stacking conductive rings 201 and insulating rings 202. Electrical connectors 203 pass through the insulating rings 202 and are electrically connected to one or more conductive ring 201 as required. A tension screw 204 screws into tension nut 205 to retain the stack together to form a core. Lock ring 206 and base 207 lock together to secure the core to a compliant mounting element 208. Plug nut 209 is secured to the end of tension nut 205.

Figure 17:
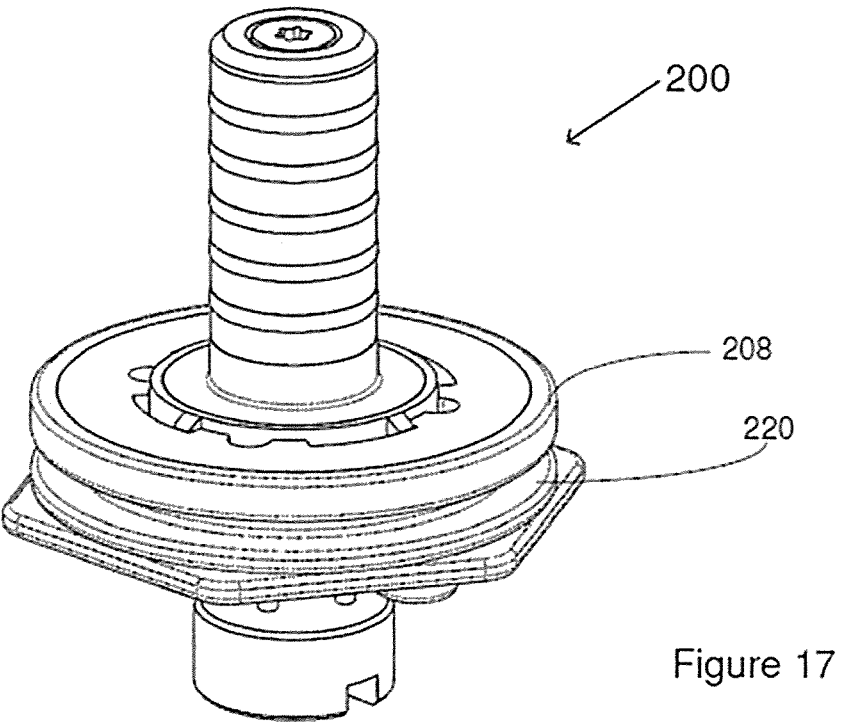
FIG. 17 shows a perspective view of the rotary connector of FIG. 16 attached to a compliant mounting element.
Figure 18:
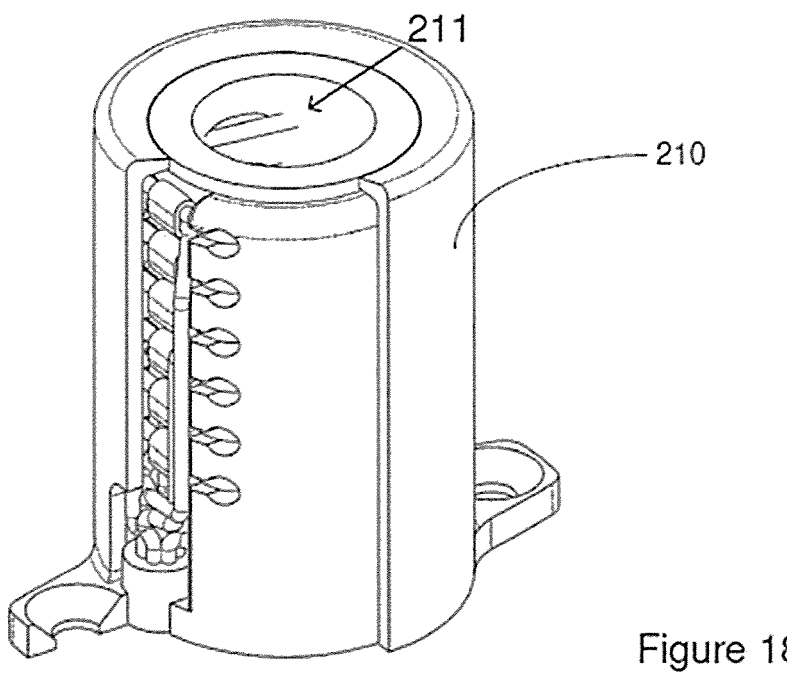
FIG. 18 shows a rotary connector housing.
Figure 19:
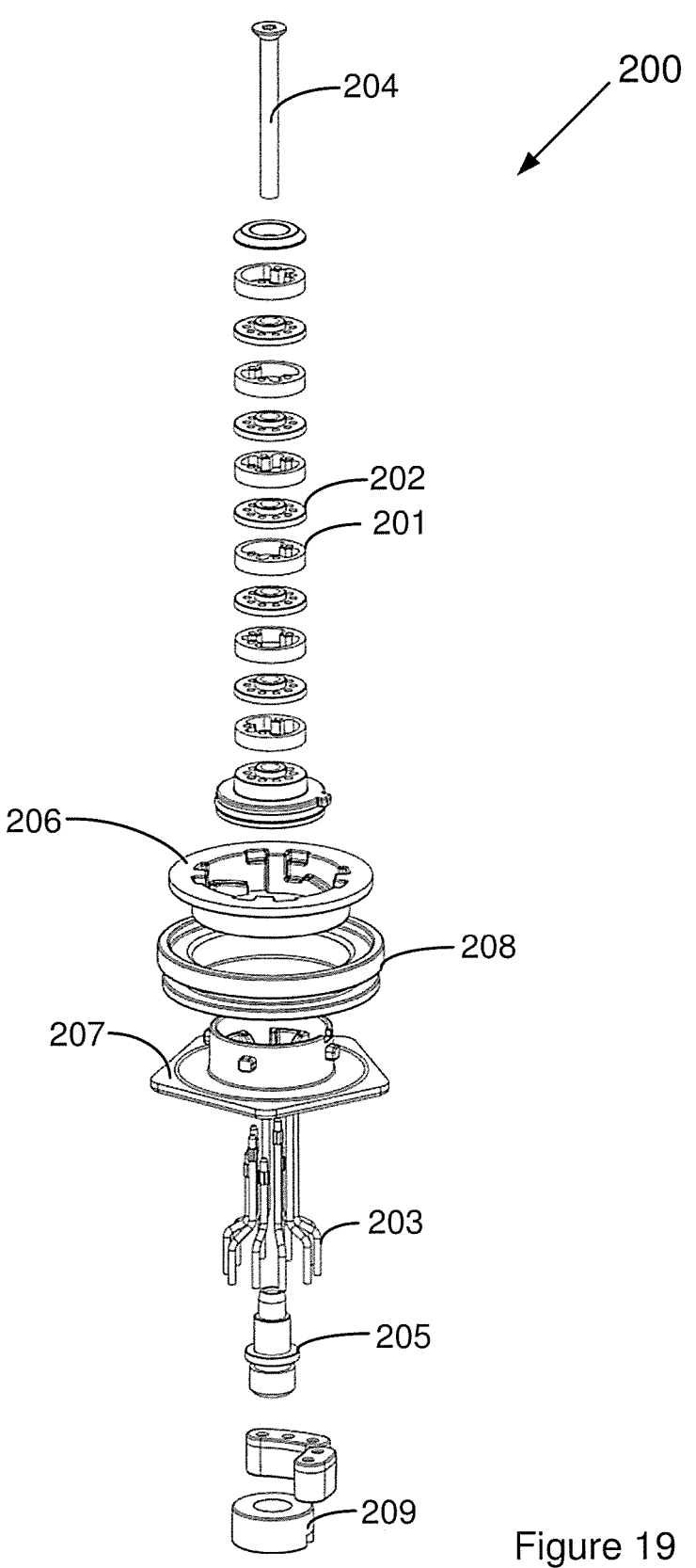
FIG. 19 shows an exploded view of the rotary connector core of FIG. 16.

The assembled rotary connector core 200 with a compliant mounting element 208 is shown in FIG. 17. The rotary connector core 200 engages with the bore 211 of a rotary connector housing 210 of a prosthesis coupling.

Figure 16:
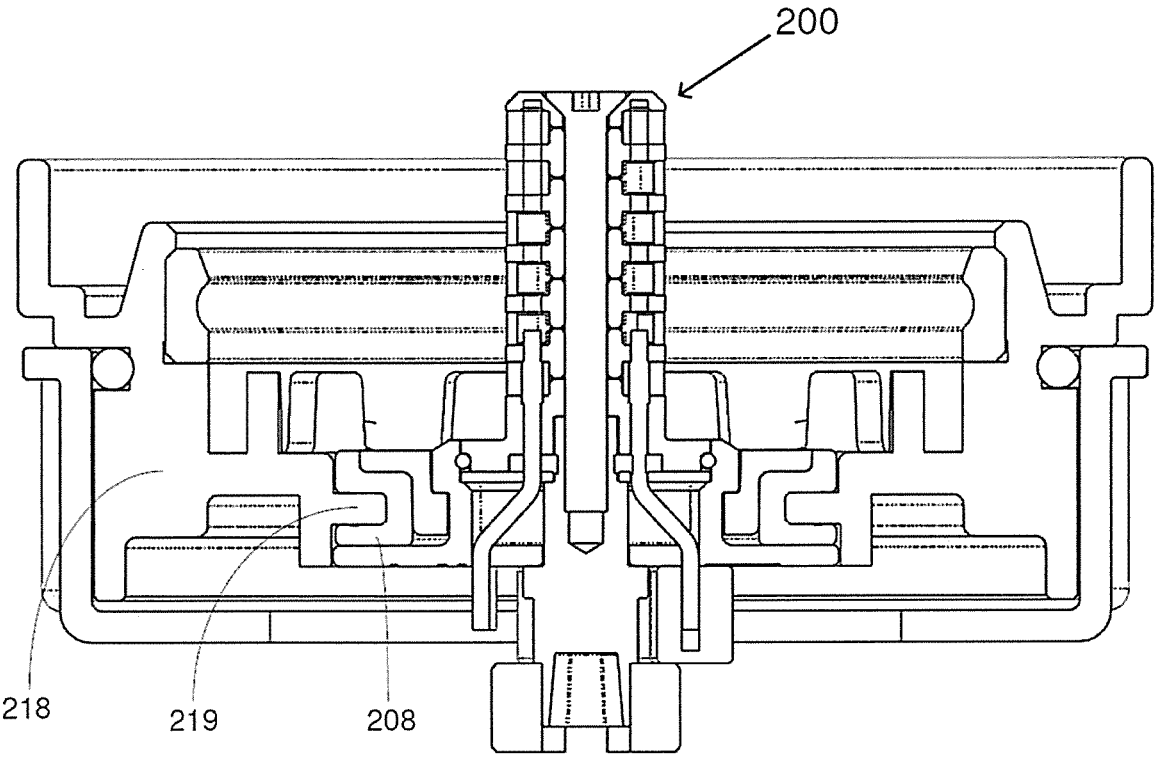
FIG. 16 shows an example rotary connector core compliantly mounted to a socket coupling.

Referring to FIG. 16 a rotary connector core 200 is shown mounted to a socket coupling 218 by a compliant mounting element 208. A recess 220 formed in compliant mounting element 208 engages with flange 219 of socket coupling 218 to provide a compliant mounting arrangement of the rotary connector core 200 relative to socket coupling 218. This allows a degree of movement of the rotary connector core 200 relative to socket coupling 218 during coupling to avoid damage to the rotary connector core 200.

The rotary connector core 200 is designed to preferentially flex and/or deform at the compliant mounting element 208 which may suitably be formed of a material having a DMTA damping factor of between 0.05 to 0.8, preferably between 0.05 to 0.5, over a temperature range of −20° C. to 100° C. The material preferably has a resilience of between 20% to 60% and a Shore A hardness of between 10 to 90 (more preferably a Shore A hardness of between 30 to 60) or alternatively a Shore D hardness of between 40 to 90. The compliant mounting element preferably provides impact absorption for forces applied to the connector core in a direction normal to the central axis such that the connector core may deviate by at least 5 degrees (preferably 10 degrees and more preferably 15 degrees) relative to the central axis due to elastic deformation of the mounting block. A force of between 2.5 and 20 Newtons applied laterally or normal to the tip of the connector core preferably results in angular rotation with respect to the central axis of at least 3 degrees, preferably at least 5 degrees, due to elastic deformation of the mounting block. The mounting block may be formed of elastomers, rubber, silicone, compressible polymers or thermoplastics materials. Preferably the material is a thermoset elastomer (either hydrocarbon, fluorocarbon or silica-based), a thermoplastic elastomer, a thermoset rubber, an inherently soft thermoplastic. It may also be an alloy or blend or a foamed composition of any of the above polymers.

The compliant mounting arrangement may allow non-destructive movement of the rotary core with respect to the socket coupling without causing damage to the rotary connector core 200. In one example the compliant mounting element 208 may allow the rotary connector core 200 to non-destructively deflect by more than 15 degrees with respect to the socket coupling. Advantageously in this example the compliant mounting element 208 may also provide a waterproof seal between the rotary connector core and the socket body. The seal is preferably waterproof to any one of the standards, IPx5, IPx6, IPx6K, IPx7 or IPx8.

Figure 20A:
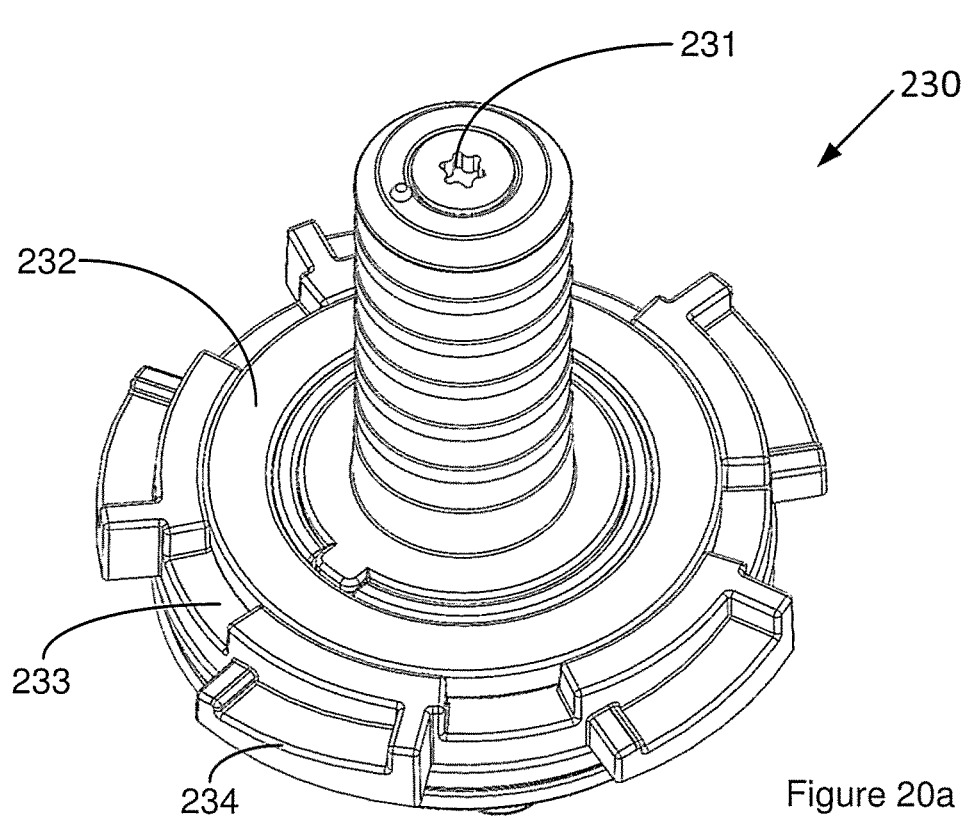
FIGS. 20*a* and 20*b* show an example connection between a rotary connector core and a socket coupling.
Figure 20B:
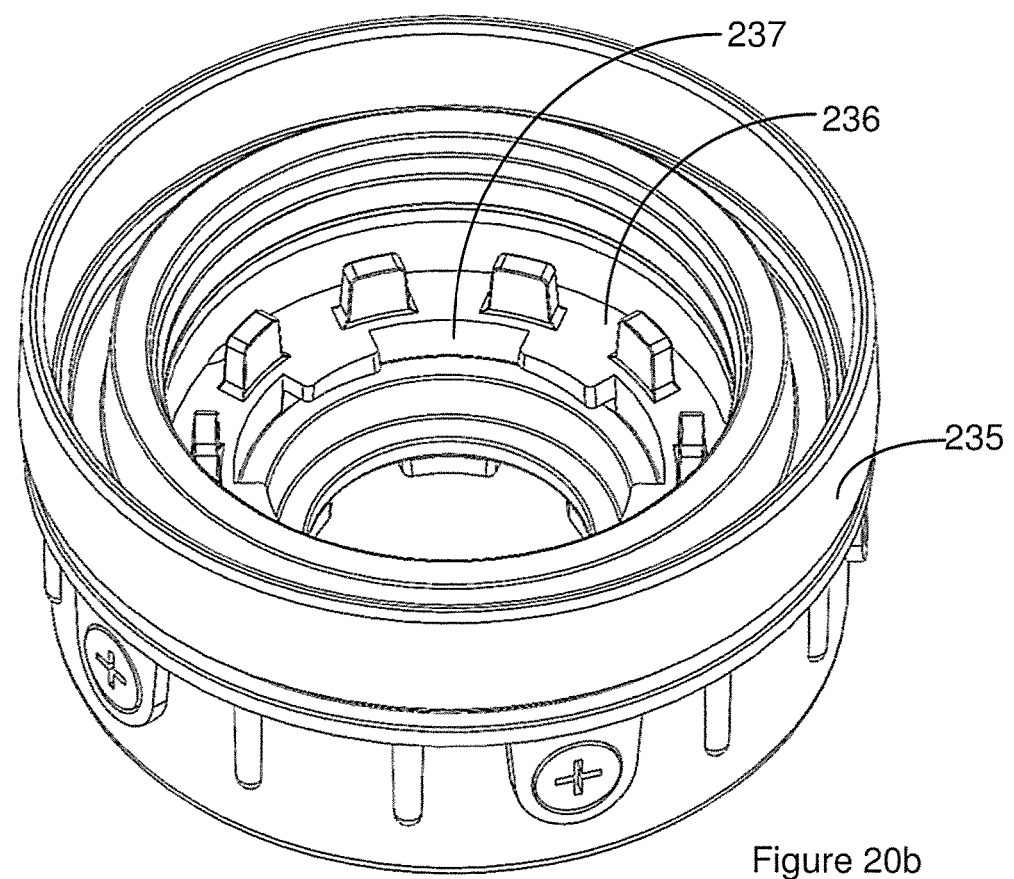

Referring to FIGS. 20a and 20b a further example of a compliant mount, rotary connector core and socket coupling will be described. A first part 230 includes a rotary connector core 231 secured to a compliant mount 232 and a mounting ring 233 secured to the compliant mount 232. The compliant mount has the properties of the compliant mount described above. The mounting ring has a number of projections 234 dimensioned to fit within notches 237 in the complementary mounting ring 236 of socket 235. This allows first part 230 to be engaged with socket coupling 235 from its distal end simply by inserting it so that projections 234 are aligned with notches 237 and then pushing and rotating the first part with respect to the socket coupling 235 in twist-lock fashion to secure the mounting rings together.

It will be appreciated that the compliant mount could be secured to the socket coupling with mounting rings provided at the interface between the rotary connector core 231 and the compliant mount 232. It will also be appreciated that the mounting rings may employ a variety of interengagement techniques, such as a screw thread, bayonet fitting, push fit etc.

In other examples compliance may be provided within the rotary connector core itself. For example a compliant material could be provided between base 207 and lock ring 206. In other examples compliance may be provided within socket coupling 218, for example by providing a compliant material between the socket coupling 218 and a rigid surface to which a rotary connector core is mounted.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A prosthesis coupling configured to rotatably and releasably engage with a race of a socket coupling, the prosthesis coupling comprising:
   a. a first sleeve including a first annular ball race section;
   b. a second sleeve having a second annular ball race section; and
   c. bearings provided within a race formed by the first ball race section and the second ball race section;
      wherein the first and second sleeves may be relatively moved such that:
      i. in a first configuration, in which the first ball race section and the second ball race section are brought together, the bearings are constrained to an outer annular zone, preventing removal of the prosthesis coupling when engaged with a socket coupling; and
      ii. in a second configuration, in which the first ball race section and the second ball race section are moved apart, the bearings may move to an inner annular zone, allowing removal of the prosthesis coupling from a prosthesis socket.

2. A prosthesis coupling as claimed in claim 1 wherein the first and second sleeves are relatively rotatable and have ramp sections configured such that upon relative rotation of the inner and outer sleeves the spacing between the first ball race section and the second ball race section may be varied.

3. A prosthesis coupling as claimed in claim 1 wherein a locking mechanism prevents relative movement between the first and second sleeves unless actuated.

4. A prosthesis coupling as claimed in claim 3 wherein the locking mechanism engages with locking features provided on the sleeves in its locking position to prevent relative rotation with respect to the other sleeve.

5. A prosthesis coupling as claimed in claim 4 wherein the locking mechanism moves axially between the locking position and an unlocked position.

6. A prosthesis coupling as claimed in claim 4 wherein the locking mechanism moves transversely to the axis of the coupling between the locking position and an unlocked position.

7. A prosthesis coupling as claimed in claim 4 wherein the locking mechanism rotates relative to the socket coupling between locked and an unlocked positions.

8. A prosthesis coupling as claimed in claim 4 wherein the locking mechanism is in the form of a locking ring having a plurality of axial projections which engage with a plurality of locking features provided on the sleeves.

9. A prosthesis coupling as claimed in claim 8 wherein the locking ring is moved axially between locked and unlocked positions by the movement of opposing first and second ramps and a linkage between the locking ring and the second ramp.

10. A prosthesis coupling as claimed in claim 9 wherein a button is linked to the first ramp and configured so that movement of the button effects relative movement between the first and second ramps.

11. A prosthesis coupling as claimed in claim 10 wherein a plurality of buttons are connected to respective ramps.

12. A prosthesis coupling as claimed in claim 3 wherein the locking mechanism engages features of both the first and second sleeves to prevent relative rotation between the sleeves.

13. A prosthesis coupling as claimed in claim 12 wherein the locking mechanism is a pin movable relative to the sleeves between a first position in which the pin engages features of the first and second sleeves to prevent rotation and a second position in which relative rotation of the sleeves is allowed.

14. A prosthesis coupling as claimed in claim 13 wherein the features are apertures in the sleeves.

15. A prosthesis coupling as claimed in claim 1 wherein an actuating mechanism moves the first and second sleeves relatively in the axial direction between the first and second configurations.

16. A prosthesis coupling as claimed in claim 15 where the actuating mechanism is in the form of a lever and cam arrangement.

17. A prosthesis coupling as claimed in claim 1 wherein the bearings are ball bearings.

18. A prosthesis coupling as claimed in claim 1 wherein the first and second sleeves are biased towards the second configuration.

19. A prosthesis coupling as claimed in claim 18 wherein a spring biases the first and second sleeves towards the second configuration.

20. A prosthesis coupling as claimed in claim 19 wherein a torsion spring biases the first and second sleeves towards the second configuration.

21. A prosthesis coupling as claimed in claim 20 wherein a helical torsion spring biases the first and second sleeves towards the second configuration.

22. A prosthesis coupling as claimed in claim 21 wherein the helical torsion spring is provided within the first sleeve and includes a leg passing through a slot in the first sleeve to engage with the second sleeve.

23. A prosthesis coupling as claimed in claim 1 further comprising a bearing cage, wherein the bearings are retained within a region defined by the first and second ball race sections and the bearing cage.

24. A prosthesis coupling configured to rotatably and releasably engage with a race of a socket coupling, the prosthesis coupling comprising:

a. a body having an annular section;

b. a first annular ball race section provided on the annular section;

c. a second annular ball race section movable between first and second positions on the annular section;

d. bearings provided within a race formed by the first ball race section and the second ball race section; and e. a release actuator movable in a first direction with respect to the body to move the second annular ball race section between:

i. a first configuration in which the first ball race section and the second ball race section are brought together such that the bearings are constrained to an outer annular zone, preventing removal of the connector when engaged with a socket coupling; and ii. a second configuration in which the first ball race section and the second ball race section are moved apart such that the bearings may move to an inner annular zone, allowing removal of the prosthesis coupling from a socket coupling;

wherein the release actuator is hand operated.

25. A prosthesis coupling as claimed in claim 24 further comprising a bearing cage, wherein the bearings are retained within the race of the prosthesis coupling by the bearing cage.

* * * * *